US012801485B2

(12) United States Patent
Chen et al.

(10) Patent No.: US 12,801,485 B2
(45) Date of Patent: Nov. 17, 2026

(54) LOG REPRESENTATION LEARNING FOR AUTOMATED SYSTEM MAINTENANCE

(71) Applicant: NEC Laboratories America, Inc., Princeton, NJ (US)

(72) Inventors: Zhengzhang Chen, Princeton Junction, NJ (US); Lecheng Zheng, Monmouth Junction, NJ (US); Haifeng Chen, West Windsor, NJ (US); Yanchi Liu, Monmouth Junction, NJ (US); Xujiang Zhao, Hillsborough, NJ (US); Yuncong Chen, Jersey City, NJ (US); LuAn Tang, Cranbury, NJ (US)

(73) Assignee: NEC Corporation, Tokyo (JP)

( * ) Notice: Subject to any disclaimer, the term of this patent is extended or adjusted under 35 U.S.C. 154(b) by 93 days.

(21) Appl. No.: 18/829,545

(22) Filed: Sep. 10, 2024

(65) Prior Publication Data

US 2025/0094271 A1 Mar. 20, 2025

Related U.S. Application Data

(60) Provisional application No. 63/542,424, filed on Oct. 4, 2023, provisional application No. 63/539,548, filed on Sep. 20, 2023.

(51) Int. Cl.

| | |
|---|---|
| ***G06F 11/07*** | (2006.01) |
| ***G06N 3/08*** | (2023.01) |
| ***G16H 10/60*** | (2018.01) |

(52) U.S. Cl.

CPC ...... *G06F 11/0793* (2013.01); *G06F 11/0709* (2013.01); *G06N 3/08* (2013.01); *G16H 10/60* (2018.01)

(58) Field of Classification Search

CPC ............. G06F 11/3006; G06F 11/0709; G06F 11/3476; G06F 11/0793; G06F 2201/81;

(Continued)

(56) References Cited

U.S. PATENT DOCUMENTS

2021/0196576 A1 7/2021 Vinograd et al.
2022/0405592 A1* 12/2022 Niu ........................ G06N 3/045

(Continued)

FOREIGN PATENT DOCUMENTS

CN 116110570 A * 5/2023 ............. G16H 10/60

OTHER PUBLICATIONS

Du et al. "DeepLog: Anomaly Detection and Diagnosis from System Logs through Deep Learning" CCS '17: Proceedings of the 2017 ACM SIGSAC Conference on Computer and Communications Security; pp. 1285-1298; 2017.*

(Continued)

*Primary Examiner* — Igor N Borissov
(74) *Attorney, Agent, or Firm* — Vincent Duffy

(57) ABSTRACT

Systems and methods for log representation learning for automated system maintenance. An optimized parser can transform collected system logs into log templates. A tokenizer can tokenize the log templates partitioned into time windows to obtain log template tokens. The log template tokens can train a language model (LM) with deep learning to obtain a trained LM. The trained LM can detect anomalies from system logs to obtain detected anomalies. A corrective action can be performed on a monitored entity based on the detected anomalies.

20 Claims, 6 Drawing Sheets

(58) Field of Classification Search
CPC .... G06F 2201/835; G06N 3/08; G06N 3/044; G16H 10/60
USPC .............................................................. 705/3
See application file for complete search history.

(56) References Cited

U.S. PATENT DOCUMENTS

| | | | | |
|---|---|---|---|---|
| 2023/0177380 | A1* | 6/2023 | Bansal | G06N 20/00 706/12 |
| 2023/0376589 | A1 | 11/2023 | Chen et al. | |

OTHER PUBLICATIONS

Meng et al. "LogAnomaly: Unsupervised Detection of Sequential and Quantitative Anomalies in Unstructured Logs" Proceedings of the Twenty-Eighth International Joint Conference on Artificial Intelligence (IJCAI-19); pp. 4739-4745; 2019.*
Guo et al. "LogBERT: Log Anomaly Detection via BERT", Utah State University, Logan UT; pp. 1-13; 2021.*
Devlin, J. (Oct. 11, 2018). Bert: Pre-training of deep bidirectional transformers for language understanding. arXiv preprint arXiv:1810.04805.
He, P., Zhu, J., Zheng, Z., & Lyu, M. R. (Jun. 25, 2017). Drain: An online log parsing approach with fixed depth tree. In 2017 IEEE international conference on web services (ICWS) (pp. 33-40). IEEE.
Li, Y., Liu, Y., Wang, H., Chen, Z., Cheng, W., Chen, Y., . . . & Liu, C. (Dec. 1, 2023). Glad: Content-aware dynamic graphs for log anomaly detection. In 2023 IEEE International Conference on Knowledge Graph (ICKG) (pp. 9-18). IEEE.
Zheng, L., Chen, Z., Wang, D., Deng, C., Matsuoka, R., & Chen, H. (Jun. 8, 2024). LEMMA-RCA: A Large Multi-modal Multi-domain Dataset for Root Cause Analysis. arXiv preprint arXiv:2406.05375.
Zheng, L., Chen, Z., He, J., & Chen, H. (May 13, 2024). MULAN: Multi-modal Causal Structure Learning and Root Cause Analysis for Microservice Systems. In Proceedings of the ACM on Web Conference 2024 (pp. 4107-4116).
Zheng, L., Chen, Z., He, J., & Chen, H. (Feb. 4, 2024). Multi-modal Causal Structure Learning and Root Cause Analysis. arXiv preprint arXiv:2402.02357.

* cited by examiner

LOG REPRESENTATION LEARNING FOR AUTOMATED SYSTEM MAINTENANCE

RELATED APPLICATION INFORMATION

This application claims priority to U.S. Provisional App. No. 63/539,548 filed on Sep. 20, 2023; U.S. Provisional App. No. 63/542,424 filed on Oct. 4, 2023, incorporated herein by reference in its entirety.

BACKGROUND

Technical Field

The present invention relates to artificial intelligence for information technology operations (AIOPs), and more particularly to log representation learning for automated system maintenance.

Description of the Related Art

Current cloud systems interconnect numerous computing nodes to provide robust, scalable, online workflow processes. Because of the large number of computing nodes and processes generated, current cloud systems produce enormous amounts of data. Such data can be used to determine the status of a cloud system concerning a system failure. However, finding a vulnerability within the cloud system using such data to diagnose a system failure would be a difficult task. Additionally, due to the immense scale of cloud systems, a significant amount of time and resources would be allotted to identify, solve, and prevent such issues.

SUMMARY

According to an aspect of the present invention, a computer-implemented method for log representation learning for automated system maintenance is provided, including, transforming collected system logs into log templates using an optimized parser, tokenizing the log templates partitioned into time windows to obtain log template tokens, training a language model (LM) with deep learning using the log template tokens to obtain a trained LM, detecting anomalies from system logs using the trained LM to obtain detected anomalies, and performing a corrective action to a monitored entity based on the detected anomalies.

According to another aspect of the present invention, a system is provided, including, a memory device, and one or more processor devices operatively coupled with the memory device to transform collected system logs into log templates using an optimized parser, tokenize the log templates partitioned into time windows to obtain log template tokens, train a language model (LM) with deep learning using the log template tokens to obtain a trained LM, detect anomalies from system logs using the trained LM to obtain detected anomalies, and perform a corrective action to a monitored entity based on the detected anomalies.

According to yet another aspect of the present invention, a non-transitory computer program product is provided including a computer-readable storage medium including program code for log representation learning for automated system maintenance, wherein the program code when executed on a computer causes the computer to transform collected system logs into log templates using an optimized parser, tokenize the log templates partitioned into time windows to obtain log template tokens, train a language model (LM) with deep learning using the log template tokens to obtain a trained LM, detect anomalies from system logs using the trained LM to obtain detected anomalies, and perform a corrective action to a monitored entity based on the detected anomalies.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
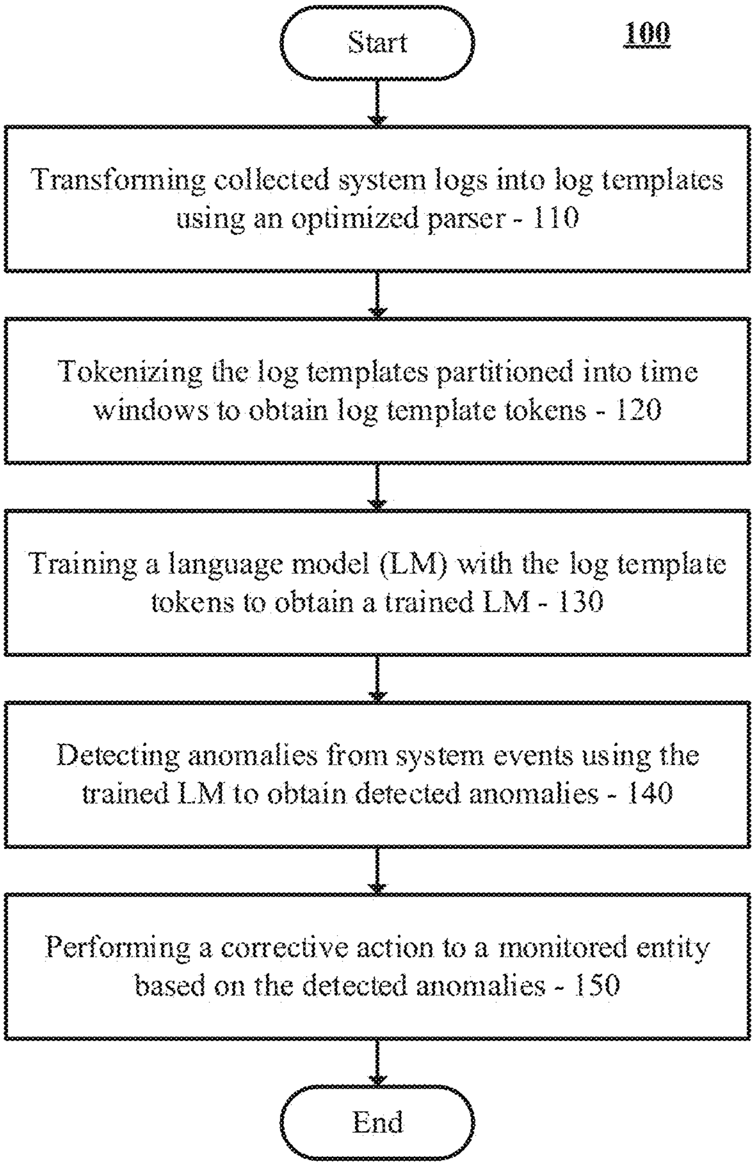
FIG. 1 is a flow diagram illustrating a high-level overview of a method for log representation learning for automated system maintenance, in accordance with an embodiment of the present invention.

In accordance with embodiments of the present invention, systems and methods are provided for log representation learning for automated system maintenance.

In an embodiment, to obtain detected anomalies, an intelligent system manager can detect anomalies from system logs using a trained language model (LM). To obtain a trained LM, log template tokens can train an LM. To obtain log template tokens, a tokenizer can tokenize log templates partitioned into time windows. An optimized parser can transform collected system logs into log templates.

The intelligent system manager can perform a corrective action to a monitored entity based on the detected anomalies. In an embodiment for a healthcare setting, the intelligent system manager can update a medical diagnosis (e.g., corrective action) of a patient (e.g., monitored entity) based on the detected anomalies from system logs, that includes the healthcare data of the patient, collected from a healthcare data system. In another embodiment for a cloud system setting, the intelligent system manager can autonomously perform system maintenance (e.g., corrective action) to update the configuration of a cloud system (e.g., monitored entity) based on the detected anomalies from system logs of the cloud system.

The surge in internet applications has ignited significant interest in microservices as a cloud-native architectural approach. This is evident for applications spanning diverse platforms, such as 5G networks, the web, and the Internet of Things (IoT). Reliable microservice performance is desired on cloud platforms, as any glitch in a microservice can lead to a diminished user experience and substantial financial repercussions. However, system failures are inevitable in intricate systems. Various factors can trigger system failures, including service level deterioration and subtle malfunctions, such as reduced throughput, increased response times, and elevated error rates.

Currently, when a microservice failure occurs, copious amounts of data, ranging from system entity metrics to system logs, events, and alerts, are collected from multiple sources. However, other system anomaly analysis models focus on utilizing metric data to construct causal graphs for system anomaly identification, and overlook the information embedded in system logs.

Consequently, effectively extracting meaningful representations from unstructured system logs for system anomaly analysis remains a formidable challenge. While a straightforward approach involves fine-tuning a pre-trained large language model with system log messages to generate representations for log sequences, system logs significantly diverge from traditional textual data due to their absence of formal grammar rules, extensive use of special tokens, and inherent lack of structure. The lack of formal grammar rules results in the difficulty in extracting the contextual information.

Consequently, mere fine-tuning of pre-trained language models on system logs can yield suboptimal representation learning. On the other hand, system logs pertaining to different entities exhibit diverse time granularities, posing a significant challenge in effectively aligning the representations to achieve uniform granularity across all entities.

The present embodiments tackle these challenges through the development of a domain-specific, language model (LM)-based log representation learning technique for automated system maintenance. The present embodiments deliver high-quality representations derived from system logs, thereby facilitating the diagnosis of failures or faults within cloud and microservice systems which is a persisting challenge within the domain of AIOps (Artificial Intelligence for IT Operations).

The present embodiments introduce a comprehensive pipeline framework that takes raw system log data as input and generates high-quality representations. This innovative technique inherently overcomes the limitations associated with directly applying a language model to system log data.

The present embodiments improve large language models for understanding system logs with a regression-based large language model trained for log representation learning, which yields log sequence representations of notably superior quality.

Other large language models consider individual words in a sentence as tokens, which complicates the learning ability of the models with keywords that are infrequently encountered and is not suitable in log sequence representation learning. Additionally, tokenizing a log template into words requires enormous amounts of memory space due to the enormous amount of data produced in a usable time window (e.g., ten to thirty minutes). Once the sequence length is larger than the maximum sequence capacity, the excess part will be ignored, resulting in information loss. A model with a larger memory capacity would result in longer training time which would be restricted in an online system with streaming data.

The present embodiments can improve the quality of log representations by employing domain-specific golden signals as label information. The present embodiments can improve system log learning by harnessing machine learning-based approaches to extract anomaly scores as label information for language model training in scenarios where domain knowledge is lacking. The present embodiments can improve the accuracy of system log representation by padding representations using previously generated representations to effectively manage diverse time scales and mitigate sparse log issues.

Referring now in detail to the figures in which like numerals represent the same or similar elements and initially to FIG. 1, a high-level overview of a method for log representation learning for automated system maintenance, is illustratively depicted in accordance with one embodiment of the present invention. Note that the reference numbers for the features described in FIG. 1 are further described in FIG. 3.

In an embodiment, to obtain detected anomalies, an intelligent system manager can detect anomalies from system logs 310 using a trained language model (LM). To obtain a trained LM 355, log template tokens (e.g., structured log representation 351) can train an LM with deep learning. To obtain log template tokens, a tokenizer can tokenize log templates partitioned into time windows. An optimized parser can transform collected system logs 310 into log templates.

The intelligent system manager 340 can perform a corrective action to a monitored entity based on the detected anomalies. In an embodiment for a healthcare setting, the intelligent system manager can update a medical diagnosis (e.g., corrective action) of a patient (e.g., monitored entity) based on the detected anomalies from system logs, that includes the healthcare data of the patient, collected from a healthcare data system. In another embodiment for a cloud system setting, the intelligent system manager 340 can autonomously perform system maintenance (e.g., corrective action) to update the configuration of a cloud system (e.g., monitored entity) based on the detected anomalies from system logs 310 of the cloud system.

In block 110, an optimized parser can transform collected system logs into log templates.

In an embodiment, an existing log parsing tool, such as the Drain™ parser, can transform unstructured system logs 310 into structured log messages represented as log event templates.

Collected system logs 310 can be unstructured due to the randomness of the log messages that can be collected. Collected system logs 310 often harbor noise and irrelevant data. To mitigate this, the Drain™ parser is optimized to eliminate noise and extraneous information, including timestamps and trace identifiers (IDs), before parsing.

In block 120, a tokenizer can tokenize the log templates partitioned into time windows to obtain log template tokens.

In an embodiment, the entire system logs 310 are partitioned into multiple time windows with fixed window size. For example, the time windows can range from ten to sixty minutes. For each time window, a log sequence is assembled, capturing unique log sequences that manifest within that specific time range.

The tokenizer can record all unique log event template in the given time windows and transform the log sequence into a sequence of event template tokens by considering each event template. The tokenizer can consider the frequency of each unique log template to determine the importance of the message it carries. For example, when a distributed denialof-service (DDOS) attack occurs, the frequency of some log event templates will suddenly increase dramatically, indicating the unusual behaviors. The tokenizer can be a large language model such as Bidirectional Encoder Representations from Transformers (BERT). Other large language models can be used.

In an embodiment, when the domain knowledge is available, the degree of abnormal log event templates existing in known signals can generate label information. For example, in the microservice system, system failures can be categorized into several categories, including a DDOS attack, storage failure, high CPU utilization, high memory utilization and etc. Each system failures have its unique key words that can identify whether a log event template is abnormal or not. The key words can include "error", "exception", "critical", "fatal", "timeout", "connection refused", "No space left on device", "out of memory", "terminated unexpectedly", "backtrace", "stack trace", "service unavailable", "502 Bad Gateway", "503 Service Unavailable", "504 Gateway Timeout", "unable to connect to", "rate limit exceeded", "request limit exceeded", "cloud system down", "cloud service not responding", "failure", "corrupted data", "data loss", "file not found", "high CPU utilization", "CPU spike", "CPU saturation", "excessive CPU usage", "failed", "shutdown", "Permission denied", "DEBUG", and etc.

In another embodiment, when the domain knowledge is not available, machine learning models can measure the abnormality of a log sequence such as transformer-based models and long short-term memory neural networks (LSTM). LSTM-based models, LSTM-based models can learn normal log patterns and detect deviations. A transformer-based approach captures contextual relationships in log sequences.

In block 130, the log template tokens can train a language model (LM) to obtain a trained LM.

In an embodiment, to train the LM 355 with deep learning, the events are converted into a learnable embedding layer to preserve relationships between system events. The embedding layer can be converted into a global loss function and a local loss function. The present embodiments can fuse the global loss function and the local loss function into a final loss function to train the LM. The structure of the LM can include sequence learning models such as gated recurrent neural networks (GRU) and LSTM. In another embodiment, a large language model (LLM) can be trained using the overall objective function. The LLM can employ a Transformer-based architecture.

Referring now to how the present embodiments can generate learnable embeddings of the system event inputs.

The inputs of the framework are the sequences of events, where each event $e_t$ is a one-hot vector and $e(j)=1$, $e(i)=0 \forall i=j$, and $e_t$ is the $j^{th}$ type event of the set $\varepsilon$. In real-world scenarios, the event space can be very large, i.e., there are tens of thousands of event types. This can lead $e_t$ to be very high-dimensional and cause notorious learning issues such as sparsity and curse of dimensionality. In addition, one-hot vector representation makes an implicit assumption that events are independent with each other, which does not hold in most cases.

The present embodiments can generate an embedding layer to embed events into a low-dimension space that can preserve relationships between system events: $E \in \mathbb{R}^{d^e \times |\varepsilon|}$, where $d^e$ is the dimension of the embedding space and $|\varepsilon|$ is the number of event types in $\varepsilon$.

With the embedding matrix, the representation of $e_t$ can be obtained as follows: $X_t = E^T \cdot e_t$, where $X_t \in \mathbb{R}^{d^e}$ is the new low-dimensional dense representation vector for $e_t$.

Referring now to how the present embodiments can generate a global loss function from the system event inputs and the learnable embeddings.

To detect an anomalous sequence, it is important to learn an effective representation of the whole sequence in the latent space. The present embodiments can integrate sequence learning models such as Gated Recurrent Neural Networks (GRU) or Long Short-Term Memory (LSTM) with a one-class objective function. Specifically, given a normal sequence, i.e., $S=(x_1, x_2, \ldots, x_N)$, the GRU learns a representation of the sequence of x in a recursive manner. At the $t^{th}$ step, the GRU outputs a state vector $h_t$, which is a linear interpolation between previous state $h_{t-1}$ and a candidate state $\tilde{h}_t$. Formally, the present embodiments can have: $h_t = z_t \odot h_{t-1} + (1-z_t) \odot \tilde{h}_t$, where $\odot$ is the element-wise multiplication; $z_t$ is the update gate, which can control how much the current state can be updated given the current information $x_t$.

$z_t$ is calculated as: $z_t = \sigma(Wx_t + Uh_{t-1})$, where W and U are the trainable parameters of the LM and $\sigma(\ )$ is a sigmoid function, which is defined as follows:

$$\sigma(x) = \frac{1}{1+e^{-x}}.$$

Moreover, the candidate state $\tilde{h}_t$ can be computed as follows: $\tilde{h}_t = g(Wx_t + U(r_t \odot h_{t-1}))$, where $g(\ )$ is the tanh function that is defined:

$$g(x) = \frac{e^x - e^{-x}}{e^x + e^{-x}};$$

and $r_t$ is the reset gate.

The reset gate can determine how much the candidate state should incorporate previous state. The reset gate is calculated as: $r_t = \sigma(Wx_t + Uh_{t-1})$.

As the state vector $h_N$ at the final step summarizes all the information in the previous steps, the present embodiments can regard it as the representation of the whole sequence.

The global loss function can be calculated as:

$$\mathcal{L}_{global} = \min_{\Theta} \frac{1}{N} \sum_{i=1}^{N} \|h_N - c\|^2 + \lambda \|\Theta\|_F^2$$

Here, c is a predefined center in the latent space and N is the total number of sequences in the training set. The first term in the objective function, $$\min_{\Theta} \frac{1}{N} \sum_{i=1}^{N} \|h_N - c\|^2,$$

employs a quadratic loss for penalizing the distance of every sequence representation to the center c and the second term, $$\lambda \|\Theta\|_F^2,$$

is a regularizer controlled by the hyperparameter $\lambda$. The global loss function can force the GRU model to map sequences to representation vectors that, on average, have the minimum distances to the center c in the latent space.

Referring now to how the present embodiments can generate a local loss function from the system event inputs and the learnable embeddings.

In an embodiment, the present embodiments model local information to consider information that is vital for anomaly detection that can be overwhelmed by other normal subsequences during the representation learning procedure.

For a given event sequence, the present embodiments can construct subsequences of a fixed size M with a sliding window. Each subsequence can contain its unique local information, that can determine whether the whole sequence is abnormal or not.

To learn the representation of the subsequences, a local GRU component can model the sequential dependencies in every subsequence. Specifically, given a subsequence $x_{t-M+1}, x_{t-M+2}, \ldots, x_t$ of length M, the local GRU can process the events sequentially and can output M hidden states, the last of which is used as the representation of the local subsequence: $h_t = \mathrm{GRU}(x_{t-M+1}, x_{t-M+2}, \ldots, x_t)$.

Thus, for all subsequences in a sequence, the GRU will obtain a sequence of hidden representations (h) that encode the sequential dependencies in every local region as follows: $h_1, h_2, \ldots, h_N = \mathrm{LocalGRU}(x_1, x_2, \ldots, x_N)$ where LocalGRU is the name for the second GRU component that processes each subsequence; and N is the number of sequences in the training set.

The present embodiments can compute the local objective function to guide the local sequence learning procedure:

$$\mathcal{L}_{local} = \min_{\theta^L} \frac{1}{N} \sum_{i=1}^{N} \sum_{j=1}^{N-M} \left\| h_{N_j^i} - c^l \right\|^2 + \lambda \|\Theta\|_F^2$$

where, $c^L$ is a predefined center of another hypersphere in the latent space, N is the number of sequences in the training set; M is the length of given subsequence, and $\theta^L$ contains all the trainable parameters of LocalGRU. Similarly, the first term penalizes the average distance between all normal subsequences to the center $c^L$ and the second term is a regularizer.

Referring now to how the present embodiments can fuse the local loss function and the global loss function to train the LM in an end-to-end manner.

Specifically, given the global and local loss functions $\mathcal{L}_{global}$ and $\mathcal{L}_{local}$, the overall objective function is defined as ${}_{\theta^L}^{min}\mathcal{L} = \mathcal{L}_{global} + \alpha \mathcal{L}_{local}$, where a is a hyper parameter that controls the contribution from local information in the sequence.

Referring now to how the present embodiments can optimize the LM.

The present embodiments can use stochastic gradient descent (SGD) and its variants (e.g., Adam) to optimize the objective function. To accelerate the training process, the predefined centers c is computed as follows: The untrained GRU can obtain the sequence representation vectors with training set sequences. The present embodiments can obtain an average vector by computing the mean value of all representation vectors and use it as c. To obtain $c^L$, a similar process is applied with untrained LocalGRU. Once c and $c^L$ are obtained, their values are fixed during the optimization process. The whole training process finishes when the objective value converges, and the trained LM can be obtained.

After training, the trained model is archived for subsequent utilization after the training phase completes. When new log data arrives, the present embodiments can fine-tune the trained LM 355 with the new incoming data for optimal performance and adaptability to obtain a fine-tuned LM 359.

In block 140, the trained LM can detect anomalies from collected system logs to obtain detected anomalies.

In an embodiment, the trained LM 355 can detect anomalies from collected system logs to obtain detected anomalies. In another embodiment, the fine-tuned LM 359 can detect anomalies from collected system logs to obtain detected anomalies. To detect anomalies for a given sequence, the present embodiments can calculate the loss defined in the overall objective function as its anomaly score. The higher the value, the more likely the given sequence being an anomaly. The present embodiments can define a set of thresholds, and then utilize the validation dataset to evaluate the model's performance under each dataset. The optimal threshold can have the best result based on the pre-defined evaluation metric. To determine the optimal threshold, precision and recall can be balanced with a measurement such as F1-score. The optimal threshold ranges from zero to one. In another embodiment, other measurements, such as geometric mean can be used.

For scenarios where some entities produce logs more frequently, the present embodiments can align and pad the representation for all entities without providing misleading information. The present embodiments can remove entities if the amount of log event for these entities is less than a threshold or these entities produce any log event after system failure occurs. Additionally, the present embodiments can determine the starting timestamp and the ending timestamp for all entities and align these entities based on the common timestamps. Further, for entities without any log event in some timestamps, the present embodiments can pad the representation with its previous representation. When the number of missing timestamps of one entity is larger than a threshold, the present embodiments can pad the representation with the mean value of the representations from the beginning to the previous timestamp. In this way, the representation can capture both "stopped working" patterns and the abnormal behavior of "generating large amounts of log events."

In block 150, an entity management system can perform corrective action to a monitored entity based on the detected anomalies.

In an embodiment in a healthcare setting, an intelligent system manager 340 can update a medical diagnosis (e.g. corrective action) of a patient (e.g., monitored entity) based on the detected anomalies. In an embodiment in a cloud system setting, an intelligent system manager 340 can update a configuration (e.g. corrective action) of the cloud system (e.g., monitored entity), such as increasing processor utilization, increasing or decreasing network bandwidth, blocking packets from an internet protocol (IP) address, etc., based on the detected anomalies.

The present embodiments can improve the quality of log representations by employing domain-specific key words as label information. The present embodiments can improve system log learning by harnessing machine learning-based approaches to extract anomaly scores as label information for language model training in scenarios where domain knowledge is lacking. The present embodiments can improve the accuracy of system log representation by padding representations using previously generated representations to effectively manage diverse time scales and mitigate sparse log issues.

Figure 2:
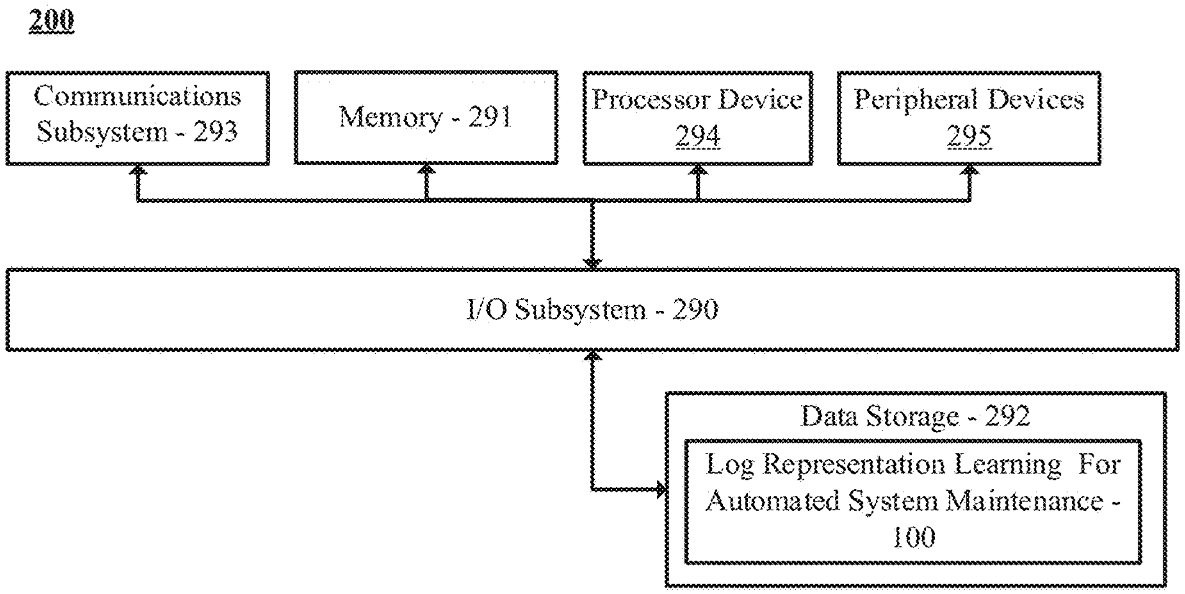
FIG. 2 is a block diagram illustrating a system for log representation learning for automated system maintenance, in accordance with an embodiment of the present invention.

Referring now to FIG. 2, a system for log representation learning for automated system maintenance is illustratively depicted in accordance with an embodiment of the present invention.

The computing device 200 illustratively includes the processor device 294, an input/output (I/O) subsystem 290, a memory 291, a data storage device 292, and a communication subsystem 293, and/or other components and devices commonly found in a server or similar computing device. The computing device 200 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 291, or portions thereof, may be incorporated in the processor device 294 in some embodiments.

The processor device 294 may be embodied as any type of processor capable of performing the functions described herein. The processor device 294 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 291 may be embodied as any type of volatile or non-volatile memory or data storage capable of performing the functions described herein. In operation, the memory 291 may store various data and software employed during operation of the computing device 200, such as operating systems, applications, programs, libraries, and drivers. The memory 291 is communicatively coupled to the processor device 294 via the I/O subsystem 290, which may be embodied as circuitry and/or components to facilitate input/output operations with the processor device 294, the memory 291, and other components of the computing device 200. For example, the I/O subsystem 290 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 290 may form a portion of a system-on-a-chip (SOC) and be incorporated, along with the processor device 294, the memory 291, and other components of the computing device 200, on a single integrated circuit chip.

The data storage device 292 may be embodied as any type of device or devices configured for short-term or long-term storage of data such as, for example, memory devices and circuits, memory cards, hard disk drives, solid state drives, or other data storage devices. The data storage device 292 can store program code for log representation learning for automated system maintenance 100. Any or all of these program code blocks may be included in a given computing system.

The communication subsystem 293 of the computing device 200 may be embodied as any network interface controller or other communication circuit, device, or collection thereof, capable of enabling communications between the computing device 200 and other remote devices over a network. The communication subsystem 293 may be configured to employ any one or more communication technology (e.g., wired or wireless communications) and associated protocols (e.g., Ethernet, InfiniBand®, Bluetooth®, Wi-Fi®, WiMAX, etc.) to affect such communication.

As shown, the computing device 200 may also include one or more peripheral devices 295. The peripheral devices 295 may include any number of additional input/output devices, interface devices, and/or other peripheral devices. For example, in some embodiments, the peripheral devices 295 may include a display, touch screen, graphics circuitry, keyboard, mouse, speaker system, microphone, network interface, and/or other input/output devices, interface devices, GPS, camera, and/or other peripheral devices.

Of course, the computing device 200 may also include other elements (not shown), as readily contemplated by one of skill in the art, as well as omit certain elements. For example, various other sensors, input devices, and/or output devices can be included in computing device 200, depending upon the particular implementation of the same, as readily understood by one of ordinary skill in the art. For example, various types of wireless and/or wired input and/or output devices can be employed. Moreover, additional processors, controllers, memories, and so forth, in various configurations can also be utilized. These and other variations of the computing system 200 are readily contemplated by one of ordinary skill in the art given the teachings of the present invention provided herein.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service.

The cloud system can have at least the following characteristics: on-demand self-service, broad network access, resource pooling, rapid elasticity, and measured service. The cloud system can have at least the following Service Models: Software as a Service (SaaS), Platform as a Service (PaaS), and Infrastructure as a Service (IaaS). The cloud system can have at least the following Deployment Models: private cloud, community cloud, public cloud, or hybrid cloud.

Figure 3:
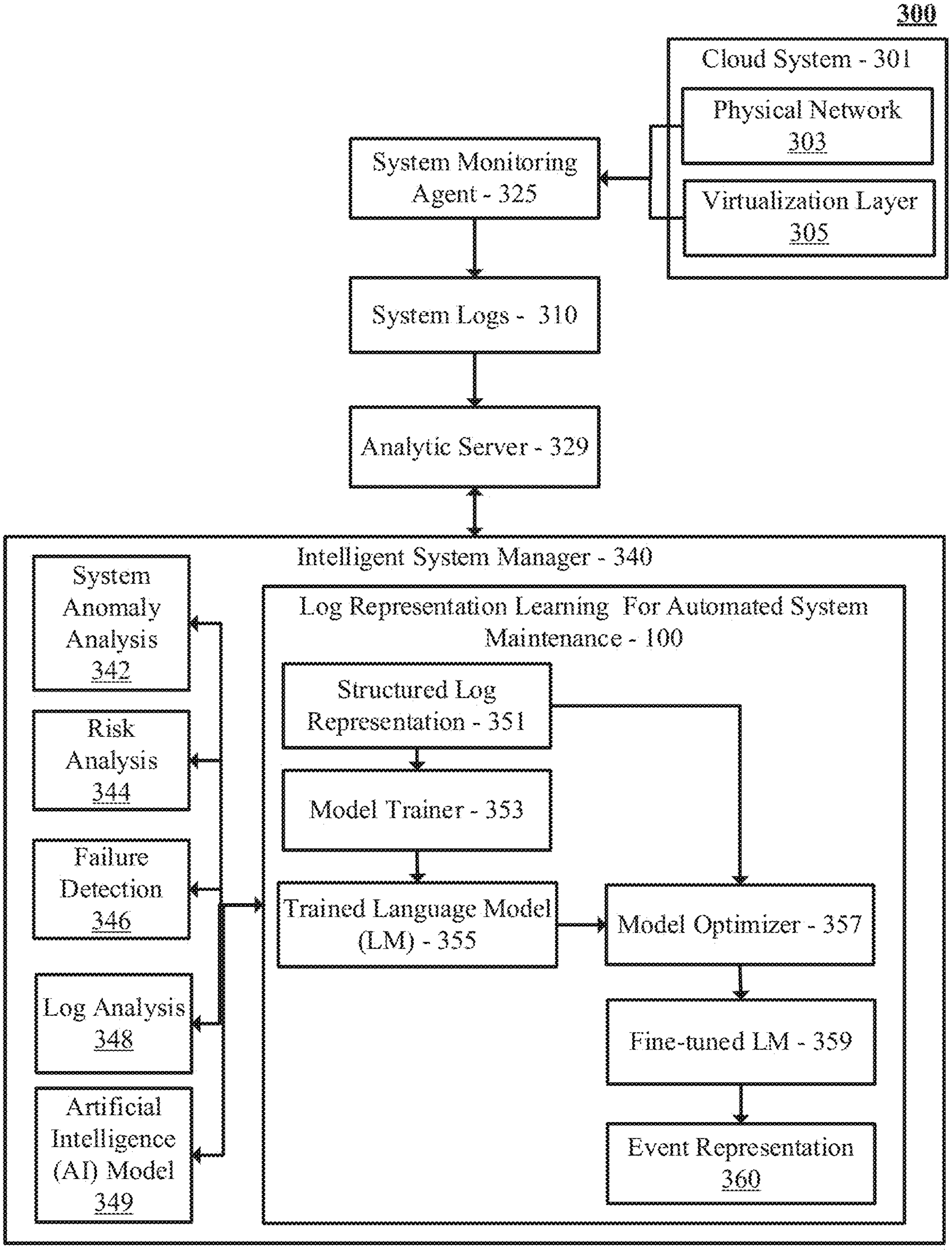
FIG. 3 is a block diagram illustrating a cloud system implementation of log representation learning for automated system maintenance, in accordance with embodiments of the present invention.

Referring now to FIG. 3, a block diagram illustrating a cloud system implementation of a log representation learning for automated system maintenance, in accordance with embodiments of the present invention.

The cloud intelligent system architecture 300 can have several components, layers, and functions: The physical network 303 can include hardware and software components. Examples of hardware components include: mainframes, RISC (Reduced Instruction Set Computer) architecture-based servers, servers, blade servers, storage devices, and networks and networking components. In some embodiments, software components include network application server software and database software.

The virtualization layer 305 provides an abstraction layer from which the following examples of virtual entities may be provided: virtual servers, virtual storage, virtual networks, including virtual private networks, virtual applications, operating systems, and virtual clients.

In an example, the management layer may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer provides examples of functionality for which the cloud computing environment may be utilized. Examples of workloads and functions which may be provided from this layer include software development and lifecycle management, data analytics processing, and transaction processing.

In an embodiment, the data analytics processing in workloads layer can include the system monitoring agent 325, analytics server 329 and the intelligent system manager 340.

In an embodiment, the cloud system 301 and analytics server 329 can be positioned in geographically different locations and interconnected by networks. In another embodiment, the cloud system 301, and analytics server 329 can be positioned in the same geographical location and interconnected by networks.

The analytics server 326 can include hardware and software components. Examples of hardware components include: mainframes, RISC architecture-based servers, servers, blade servers, storage devices, and networks and networking components. In some embodiments, software components include network application server software and database software.

In an embodiment, the intelligent system manager 340 can include system anomaly analysis module 342, a risk analysis module 344, a failure detection module 346, and a log analysis module 348. The intelligent system manager 340 can include a log representation learning for automated system maintenance 100. The system anomaly analysis module 342 can pinpoint the system anomaly of a system failure from the entities (e.g., container, node, etc.) of a cloud system based on the detected system anomalies.

The detected system anomalies, through the failure detection module 346, can have identifiable sources and timestamps on which point and batch of processing the detected system anomaly for system failure occurred (e.g., batch processing data). The source identifier, timestamp, batch processing data can be compiled and converted to a complete sentence to produce an explanation of how a system fault or failure occurred due to the detected system anomaly for system failure. In another embodiment, the conversion to complete sentences can be done by an artificial intelligence (AI) model 349.

In another embodiment, the intelligent system manager 340 can perform log analysis and process the logs produced in the cloud system and detect system anomalies for system failures within the cloud system through the logs. The intelligent system manager 340 can generate alerts regarding system failures identified in the logs. Once a log has been identified that was related to the predicted system anomaly for system failure, the intelligent system manager 340 can autonomously perform a system maintenance to avoid a potential system failure from the log. The log analysis module 348 can include the log parser and tokenizer.

In another embodiment, the intelligent system manager 340 through the risk analysis module 344 can perform risk analysis by analyzing the detected system anomalies to identify the potential issues and consequences associated with the detected system anomalies. The identified potential issues can be assessed to evaluate their severity and likelihood of occurrence. The identified potential issues can be ranked based on severity and likelihood of occurrence which can be presented to the cloud system professional to help with their decision making.

The intelligent system manager 340 can include an AI model 349 to learn the detected system anomalies and predict the system vulnerabilities or issues that may be caused by the detected system anomalies. The intelligent system manager 340 can employ the AI model 349 to also predict appropriate fixes to the predicted system vulnerabilities and issues that may be caused by the detected system anomalies. The AI model 349 can be autoencoders, gaussian mixture models, graph neural networks, Bayesian networks, etc. Other artificial intelligence frameworks are contemplated.

The intelligent system manager 340 can be included in an analytics server 329.

The system monitoring agent 325 can monitor the cloud system 301 by monitoring the system logs 310 of the cloud system. The system logs 310 of the cloud system can include key performance indicator (KPI) data such as connect time data and latency data. The system logs 310 of the cloud system can include network metrics data that indicates the status of a cloud system's underlying component/entity such as memory utilization data and central processing unit (CPU) utilization data. The log representation learning for automated system maintenance 100 can transform system logs 310 to structured log representation 351. A model trainer 353 can train an LM using the structured log representations 351 to obtain a trained LM 355. A model optimizer 357 can fine-tune the trained LM 355 using newly transformed structured log representation 351 from newly collected system logs 310 to obtain a fine-tuned LM 359. The fine-tuned LM 359 can generate event representations 360 which can include the detected system anomalies.

The present embodiments can improve the quality of log representations by employing domain-specific golden signals as label information. The present embodiments can improve system log learning by harnessing machine learning-based approaches to extract anomaly scores as label information for language model training in scenarios where domain knowledge is lacking. The present embodiments can improve the accuracy of system log representation by padding representations using previously generated representations to effectively manage diverse time scales and mitigate sparse log issues.

A cloud computing environment is service oriented with a focus on statelessness, low coupling, modularity, and semantic interoperability. At the heart of cloud computing is an infrastructure that includes a network of interconnected nodes.

Figure 4:
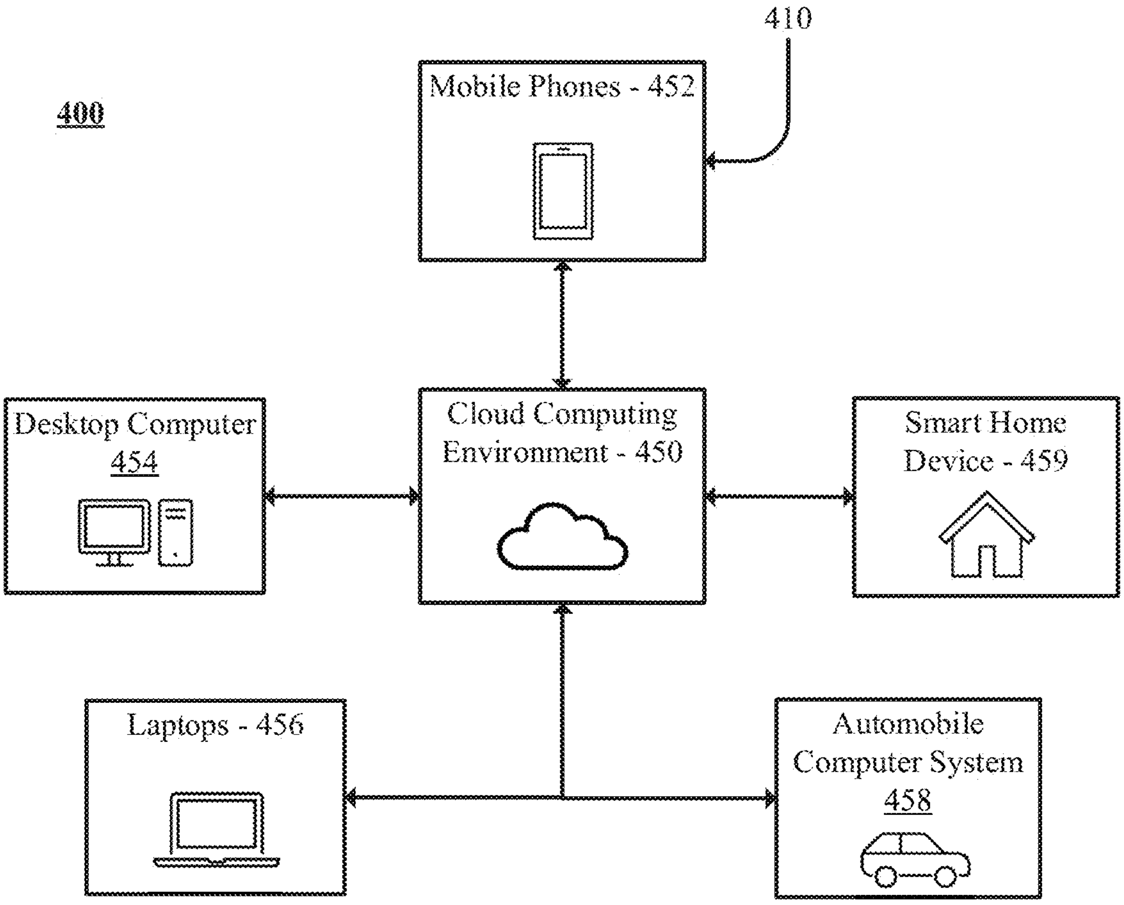
FIG. 4 is a block diagram illustrating a cloud system having cloud computing nodes that cloud consumers communicate with, in accordance with an embodiment of the present invention.

Referring now to FIG. 4, a block diagram illustrating a cloud system having cloud computing nodes that cloud consumers communicate with, in accordance with an embodiment of the present invention.

As shown, cloud system 400 can include a cloud computing environment 450 includes one or more cloud computing nodes 410 with which local computing devices used by cloud consumers, such as, for example, mobile phones 452, desktop computer 454, laptop computer 456, automobile computer system 458, and/or smart home device 459 may communicate. Nodes 410 may communicate with one another. They may be grouped (not shown) physically or virtually, in one or more networks, such as Private, Community, Public, or Hybrid clouds as described herein, or a combination thereof. This allows cloud computing environment 450 to offer infrastructure, platforms and/or software as services for which a cloud consumer does not need to maintain resources on a local computing device. It is understood that the types of computing devices 452, 454, 456, 458, 459 shown in FIG. 4 are intended to be illustrative only and that computing nodes 410 and cloud computing environment 450 can communicate with any type of computerized device over any type of network and/or network addressable connection (e.g., using a web browser).

In an embodiment, the intelligent system manager 340 can autonomously detect system anomalies from the interactions between the computing nodes 410 and cloud system 301. Based on the detected system anomalies, the system configuration of the cloud system 301 can be updated. For example, for processes concerning mobile phones 452, an anomalous latency data extracted from system logs can be identified as a system anomaly. A corresponding system maintenance plan 508 can be generated by the intelligent system manager 340 to resolve such system anomaly such as increasing bandwidth capacity of the cloud system 301 for mobile phones 452.

Figure 5:
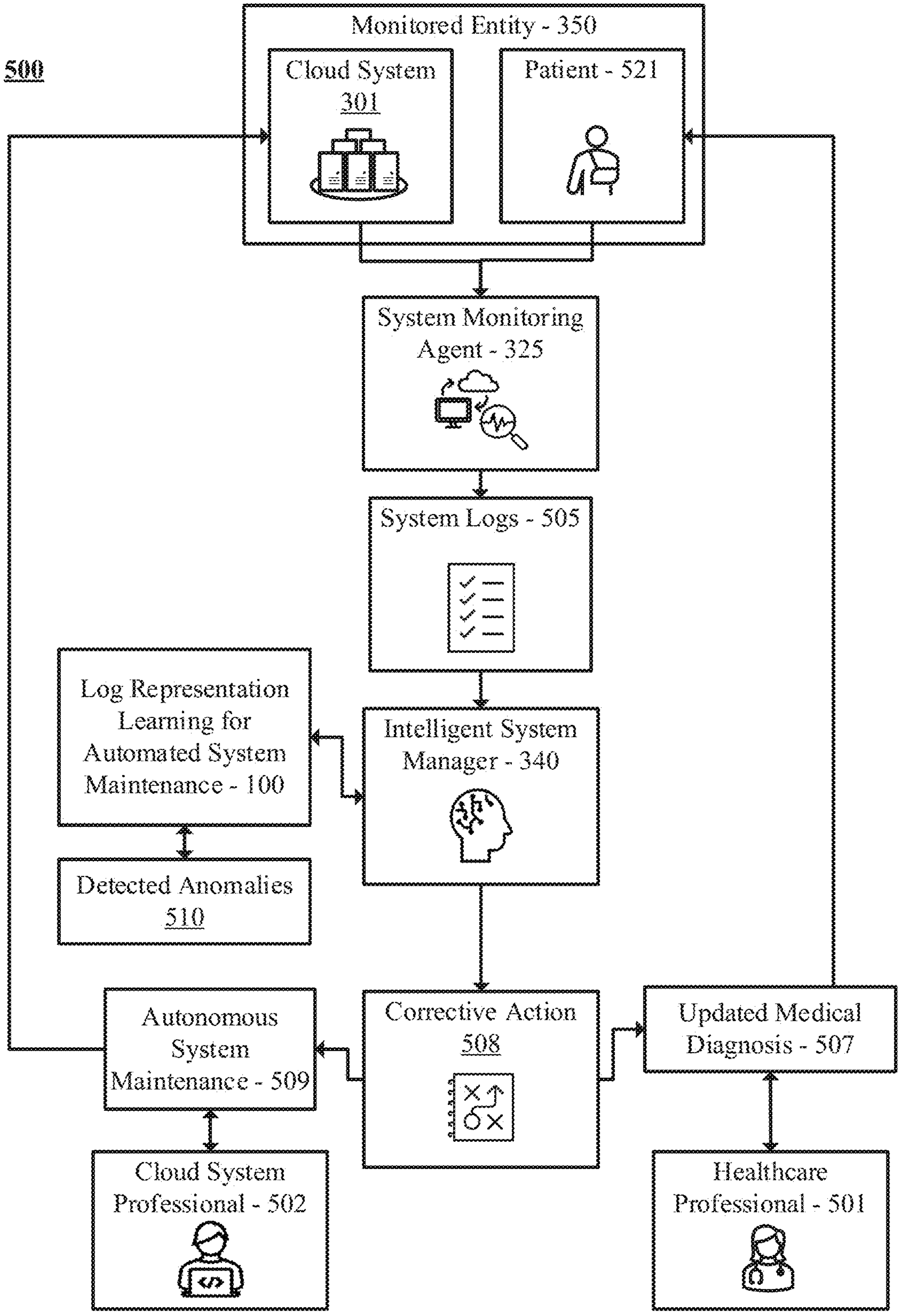
FIG. 5 is a block diagram illustrating a practical application of log representation learning for automated system maintenance, in accordance with an embodiment of the present invention.

Referring now to FIG. 5, a block diagram illustrating a practical application of a log representation learning for automated system maintenance, in accordance with an embodiment of the present invention.

In an embodiment, system 500 can include an intelligent system manager 340 that can process the detected anomalies 510 and can perform a corrective action 508.

The corrective action can be an autonomous system maintenance 509 for the cloud system 301 to resolve a system issue caused by the detected anomalies 510 based on the system logs 505 extracted by a system monitoring agent 325. The autonomous system maintenance 509 can apply system patches autonomously to the cloud system 301 to overcome a system vulnerability caused by the detected anomalies 510. The system patch can be updating hardware or software configuration in accordance with the detected anomalies 510 such as adding more CPU resources, increasing bandwidth, blocking packets from internet protocol (IP) addresses, etc.

The intelligent system manager 340 can then provide recommendations to the cloud professional 502 regarding the system maintenance plan 508 to assist with the decision-making of the cloud professional 502. The recommendation can be adding computing resources to a computing node where the system anomaly for system failure was detected. The recommendation can also be applying system patches to the cloud system 301. The recommendation can be that the intelligent system manager 340 can autonomously place the cloud system 301 under system maintenance to install the system patches. The present embodiments can install the system patches in the background without interfering with access to the cloud system 301.

In another embodiment, the intelligent system manager 340 can output explanations regarding system faults or failure based on the detected anomalies 510 as described herein. In another embodiment, the intelligent system manager 340 can perform risk analysis by analyzing the detected system anomalies for system failure to identify the potential issues and consequences associated with the detected anomalies 510 as described herein.

In another embodiment, the corrective action 508 can be an updated medical diagnosis 507 of a patient 521 based on system logs 505, that includes healthcare data of the patient 521, collected from a healthcare data system. The updated medical diagnosis 507 can include updating medical treatment, updating healthcare professional 501, changing rooms, etc. In another embodiment, the updated medical diagnosis 507 can be recommended to a healthcare professional 501 to assist the decision-making process of the healthcare professional 501 regarding the health of the patient 521. Other practical applications are contemplated.

The present embodiments can improve the quality of log representations by employing domain-specific key words as label information. The present embodiments can improve system log learning by harnessing machine learning-based approaches to extract anomaly scores as label information for language model training in scenarios where domain knowledge is lacking. The present embodiments can improve the accuracy of system log representation by padding representations using previously generated representations to effectively manage diverse time scales and mitigate sparse log issues.

The present embodiments can employ a deep learning neural network (e.g., trained LM 355, AI model 349) for the intelligent system manager 340 to learn how the system anomalies occur and predict potential solutions for the issues and vulnerabilities that the system anomalies for system failures can cause.

Figure 6:
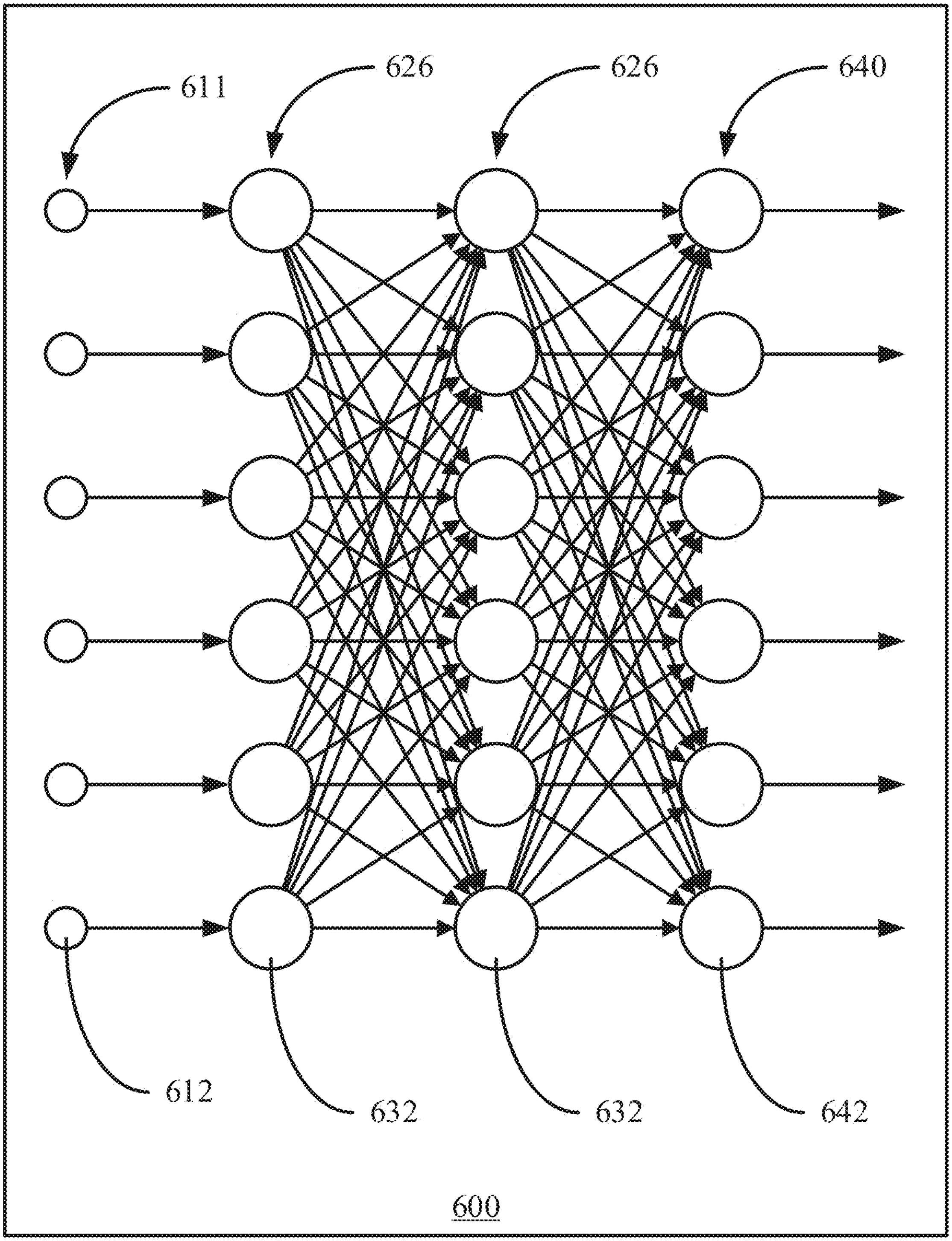
FIG. 6, a block diagram illustrating deep learning neural networks log representation learning for automated system maintenance, in accordance with an embodiment of the present invention.

Referring now to FIG. 6, a block diagram illustrating deep learning neural networks for log representation learning for automated system maintenance, in accordance with an embodiment of the present invention.

A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the inputted data belongs to each of the classes can be output.

The empirical data, also known as training data, from a set of examples can be formatted as a string of values and fed into the input of the neural network. Each example may be associated with a known result or output. Each example can be represented as a pair, (x, y), where x represents the input data and y represents the known output. The input data may include a variety of different data types and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

The deep neural network 600, such as a multilayer perceptron, can have an input layer 611 of source nodes 612, one or more computation layer(s) 626 having one or more computation nodes 632, and an output layer 640, where there is a single output node 642 for each possible category into which the input example can be classified. An input layer 611 can have a number of source nodes 612 equal to the number of data values 612 in the input data 611. The computation nodes 632 in the computation layer(s) 626 can also be referred to as hidden layers, because they are between the source nodes 612 and output node(s) 642 and are not directly observed. Each node 632, 642 in a computation layer generates a linear combination of weighted values from the values output from the nodes in a previous layer, and applies a non-linear activation function that is differentiable over the range of the linear combination. The weights applied to the value from each previous node can be denoted, for example, by $w_1, w_2, \ldots w_{n-1}, w_n$. The output layer provides the overall response of the network to the inputted data. A deep neural network can be fully connected, where each node in a computational layer is connected to all other nodes in the previous layer, or may have other configurations of connections between layers. If links between nodes are missing, the network is referred to as partially connected.

In an embodiment, the computation layers 626 of the trained LM 355 used in the intelligent system manager 340 can incrementally learn the context within collected system logs to generate structured log representations for system events in a time window. The output layer 640 of the trained LM 355 used in the intelligent system manager 340 can then provide the overall response of the network as a likelihood score of a generated structured log representations for system events occurring for the processed collected system log for a given time. In an embodiment, the fine-tuned LM 359 can generate an event representation 360 that can include detected system anomalies from collected system logs within a time window. In another embodiment, the overall response can output a predicted recommendation to resolve a system issue or vulnerability caused by the detected system anomalies for system failure.

Training a deep neural network can involve two phases, a forward phase where the weights of each node are fixed and the input propagates through the network, and a backwards phase where an error value is propagated backwards through the network and weight values are updated.

The computation nodes 632 in the one or more computation (hidden) layer(s) 626 perform a nonlinear transformation on the input data 612 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid-state memory, magnetic tape, a removable computer diskette, a random-access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art can implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method for log representation learning for automated system maintenance, comprising:

transforming collected system logs of event sequences from a monitored entity of a cloud system into log templates using an optimized parser;

tokenizing the log templates partitioned into time windows to obtain log template tokens;

training a language model (LM) with deep learning using the log template tokens including learning sequential dependencies of subsequences of the log sequences with a local gated recurrent neural network (GRU) of the LM based on a local loss function to obtain a trained LM that mitigates sparse log issues when detecting anomalies from the cloud system;

detecting anomalies from the system logs using the trained LM to obtain detected anomalies; and performing a corrective action to the monitored entity to resolve operational issues to the cloud system caused by the detected anomalies including increasing processor utilization of the cloud system.

2. The computer-implemented method of claim 1, wherein performing a corrective action further comprises updating a medical diagnosis of a patient based on the detected anomalies from system logs, that includes health-care data of the patient, collected from the cloud system.

3. The computer-implemented method of claim 1, wherein transforming collected system logs further comprises optimizing a parser to eliminate noise and extraneous information from system logs.

4. The computer-implemented method of claim 1, wherein tokenizing the log templates further comprises partitioning system logs into multiple time windows with a fixed window size to capture unique log sequences within a specific time range.

5. The computer-implemented method of claim 1, wherein training a language model further comprises fine-tuning the trained LM using Incoming system logs to optimize performance and adaptability.

6. The computer-implemented method of claim 5, wherein training a language model further comprises computing a global loss function that maps log sequences to representation vectors that have an average minimum distances to a center in a latent space in an embedding layer using a recurrent neural network.

7. The computer-implemented method of claim 6, wherein training a language model further comprises computing the local loss function that obtains a sequence of hidden representations that encode sequential dependences in local regions in the latent space.

8. The computer-implemented method of claim 7, wherein training a language model further comprises fusing the global loss function and the local loss function to obtain a fused loss function to train the LM using the fused loss function.

9. The computer-implemented method of claim 1, wherein training a language model further comprises transforming system logs into an embedding layer to preserve relationships between system logs.

10. A system, comprising:

a memory device; and one or more processor devices operatively coupled with the memory device to:

transform collected system logs of event sequences from a monitored entity of a cloud system into log templates using an optimized parser;

tokenize the log templates partitioned into time windows to obtain log template tokens;

train a language model (LM) with deep learning using the log template tokens including learning sequential dependencies of subsequences of the log sequences with a local gated recurrent neural network (GRU) of the LM based on a local loss function to obtain a trained LM that mitigates sparse log issues when detecting anomalies from the cloud system:

detect anomalies from the system logs using the trained LM to obtain detected anomalies; and perform a corrective action to the monitored entity to resolve operational issues to the cloud system caused by based on the detected anomalies including increasing processor utilization of the cloud system.

11. The system of claim 10, wherein to perform a corrective action further comprises to update a medical diagnosis of a patient based on the detected anomalies from system logs, that includes healthcare data of the patient, collected from the cloud system.

12. The system of claim 10, wherein to transform collected system logs further comprises optimizing a parser to eliminate noise and extraneous information from system logs.

13. The system of claim 10, wherein to tokenize the log templates further comprises to partition system logs into multiple time windows with a fixed window size to capture unique log sequences within a specific time range.

14. The system of claim 10, wherein to train a language model further comprises to fine-tune the trained LM using incoming system logs to optimize performance and adaptability.

15. The system of claim 10, wherein to train a language model further comprises to compute a global loss function that maps log sequences to representation vectors that have an average minimum distances to a center in a latent space in an embedding layer using a recurrent neural network.

16. The system of claim 15, wherein to train a language model further comprises computing the local loss function that obtains a sequence of hidden representations that encode sequential dependences in local regions in the latent space.

17. The system of claim 16, wherein to train a language model further comprises to fuse the global loss function and the local loss function to obtain a fused loss function to train the LM using the fused loss function.

18. The system of claim 10, wherein to train a language model further comprises transforming system logs into an embedding layer to preserve relationships between system logs.

19. A non-transitory computer program product comprising a computer-readable storage medium including program code for log representation learning for automated system maintenance, wherein the program code when executed on a computer causes the computer to:

transform collected system logs of event sequences from a monitored entity of a cloud system into log templates using an optimized parser;

tokenize the log templates partitioned into time windows to obtain log template tokens;

train a language model (LM) with deep learning using the log template tokens including learning sequential dependencies of subsequences of the log sequences with a local gated recurrent neural network (GRU) of the LM based on a local loss function to obtain a trained LM that mitigates sparse log issues when detecting anomalies from the cloud system:

detect anomalies from the system logs using the trained LM to obtain detected anomalies; and perform a corrective action to the monitored entity to resolve operational issues to the cloud system caused by the detected anomalies including increasing processor utilization of the cloud system.

20. The non-transitory computer program product of claim 19, wherein to perform a corrective action further comprises updating a medical diagnosis of a patient based on the detected anomalies from system logs, that includes healthcare data of the patient, collected from the cloud system.

* * * * *